(12) United States Patent
Okamura et al.

(10) Patent No.: US 9,901,708 B2
(45) Date of Patent: Feb. 27, 2018

(54) INTRODUCER SHEATH

(71) Applicant: TERUMO KABUSHIKI KAISHA, Shibuya (JP)

(72) Inventors: Ryo Okamura, Fujinomiya (JP); Yushin Yazaki, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 549 days.

(21) Appl. No.: 14/492,650

(22) Filed: Sep. 22, 2014

(65) Prior Publication Data

US 2015/0011978 A1 Jan. 8, 2015

Related U.S. Application Data

(63) Continuation-in-part of application No. PCT/JP2013/055172, filed on Feb. 27, 2013.

(30) Foreign Application Priority Data

Mar. 22, 2012 (JP) ................................. 2012-066008

(51) Int. Cl.
*A61M 25/00* (2006.01)
*A61M 25/06* (2006.01)
*A61M 29/00* (2006.01)

(52) U.S. Cl.
CPC .... *A61M 25/0068* (2013.01); *A61M 25/0662* (2013.01); *A61M 29/00* (2013.01);
(Continued)

(58) Field of Classification Search
CPC .............. A61M 25/0068; A61M 29/00; A61M 25/0662; A61M 2025/0687; A61M 2025/0681
(Continued)

(56) References Cited

U.S. PATENT DOCUMENTS 8,771,245 B2 * 7/2014 Williams ............ A61M 1/0023
604/26
2009/0187098 A1 * 7/2009 Makower ............. A61B 1/0661
600/424
2010/0057018 A1 3/2010 Lentz et al.

FOREIGN PATENT DOCUMENTS

JP 61-24024 B2 6/1986
JP 7-178108 A 7/1995
(Continued)

OTHER PUBLICATIONS

International Search Report (PCT/ISA/210) dated May 28, 2013, by the Japanese Patent Office as the International Searching Authority for International Application No. PCT/JP2013/055172.

*Primary Examiner* — Vy Bui

(74) *Attorney, Agent, or Firm* — Buchanan Ingersoll & Rooney PC

(57) ABSTRACT

An introducer sheath is provided with a sheath tube which is formed of a tubular member provided with a hollow portion through which an elongated body is freely inserted and includes a distal portion having a tapering outer diameter and a main body portion having a constant outer diameter. The distal portion of the sheath tube includes a concave portion which is bent radially inward from an end portion, through which an elongated body protrudes, in a concave shape in a cross section parallel to an axial direction, and a convex portion which is contiguous to the concave portion and is bent radially outward in a convex shape in a cross section parallel to the axial direction.

6 Claims, 6 Drawing Sheets

(52) U.S. Cl.
CPC ............... *A61M 2025/0681* (2013.01); *A61M 2025/0687* (2013.01)

(58) Field of Classification Search
USPC .......................................... 606/191; 604/523
See application file for complete search history.

(56) References Cited

FOREIGN PATENT DOCUMENTS

| | | |
|---|---|---|
| JP | 8-131552 A | 5/1996 |
| JP | 2001-170183 A | 6/2001 |
| WO | WO 2010/027661 A2 | 3/2010 |

\* cited by examiner

INTRODUCER SHEATH

CROSS-REFERENCES TO RELATED APPLICATIONS

This application is a continuation-in-part of International Application No. PCT/JP2013/055172 filed on Feb. 27, 2013, and claims priority to Japanese Application No. 2012-066008 filed on Mar. 22, 2012, the entire content of both of which is incorporated herein by reference.

TECHNICAL FIELD

The present invention generally relates to an introducer sheath.

BACKGROUND DISCUSSION

In recent years, various types of treatments and examinations in the medical field have been performed using an elongated and hollow tubular-shaped medical instrument called a catheter. In such treatment methods, the following procedures in which a medical catheter is utilized using the elongated shape thereof have been performed. The treatment methods include a treatment method of directly administering an agent into an affected area using a catheter; a treatment method of extending and opening a narrowed section in the lumen in a living body using a catheter in which a balloon expanded by pressure is attached to a distal end thereof; a treatment method of scraping and opening the affected area using a catheter in which a cutter is attached to a distal portion thereof; and a treatment method of closing arterial aneurysm or bleeding sites, or a feeding vessel with a filling material using a catheter. The treatment methods further include a treatment method of embedding and placing a tubular-shaped stent which has a mesh-shaped side surface into the lumen in a living body using a catheter to maintain an open state of the narrowed section in the lumen in the living body. In addition, aspirating a thrombus that blocks a blood vessel is also included in the treatment methods.

When performing treatment, inspection, and the like using a catheter, in general, an introducer sheath is introduced into a puncture site formed in an arm or a leg using a catheter introducer, and a catheter or the like is percutaneously inserted into a lesion area in the blood vessel or the like through a lumen of the introducer sheath.

The introducer sheath is formed from a sheath tube which is a tubular member provided with a hollow portion through which an elongated body such as a catheter is freely inserted. An example is disclosed in Japanese Application Publication No. 08-131552. The introducer sheath is provided with a distal portion which becomes a distal side when introducing the introducer sheath into a puncture site; and a main body portion positioned at a proximal side of the distal

SUMMARY

It is preferable that the wall thickness of the introducer sheath be made small in order to easily puncture the skin or the blood vessel by making the outer diameter of the introducer sheath small and to make an elongated body having a large outer diameter be insertable by making the inner diameter of the introducer sheath large.

However, if the wall thickness of the introducer sheath is made small, there is a problem in that a distal portion of the introducer sheath is easily curled upward when the skin or the blood vessel is punctured by the introducer sheath. In introducer sheaths in the related art, there is no configuration in which the wall thickness is formed to be thin while preventing the distal portion from being curled upward.

The introducer sheath disclosed here can prevent the distal portion from being curled upward when introduced into a puncture site even if the wall thickness is small.

An introducer sheath which is formed of a tubular member provided with a hollow portion through which an elongated body is freely inserted, including: a distal portion which has a tapering outer diameter; and a main body portion which is located proximally of the distal portion and has a constant outer diameter, in which, the distal portion has an external shape including a concave portion which is bent radially inward from an end portion, through which an elongated body protrudes, in a concave shape in a cross section parallel to an axial direction, and a convex portion which is contiguous to the concave portion and is bent radially outward in a convex shape in a cross section parallel to the axial direction.

The external shape of the concave portion or the convex portion is a shape which is bent in a quadratic curve shape.

The external shape which is bent in the quadratic curve shape is a shape which is bent in a parabola shape.

An introducer assembly including: an introducer sheath which is formed of a tubular member provided with a hollow portion through which an elongated body is freely inserted, and includes a distal portion that has a tapering outer diameter, and a main body portion which is located proximally of the distal portion and has a constant outer diameter; and a dilator that can be inserted into the hollow portion of the introducer sheath, in which the inner diameter of the distal portion, the inner diameter of the distal portion is smaller than the inner diameter of the main body portion before the dilator is inserted into the hollow portion of the introducer sheath, and in which, when the dilator is inserted into the hollow portion of the introducer sheath and a distal end of the dilator protrudes from an end portion of the distal portion through which an elongated body protrudes, the distal portion has an external shape including a concave portion which is bent radially inward from the end portion in a concave shape in the cross section parallel to the axial direction, and a convex portion which is contiguous to the concave portion and is bent radially outward in a convex shape in the cross section parallel to the axial direction.

It is possible with the introducer sheath disclosed here to prevent the distal portion from being curled upward when introduced into a puncture site even if the wall thickness is small, with the distal portion of the introducer sheath provided with the concave portion which is bent radially inward from the end portion, through which an elongated body protrudes, in the concave shape in the cross section parallel to the axial direction, and the convex portion which is contiguous to the concave portion and is bent radially outward in the convex shape in the cross section parallel to the axial direction.

Specifically, the distal portion of the introducer sheath includes the concave portion which is bent radially inward from the end portion thereof in the concave shape, and therefore, the end portion is formed at an acute angle. Accordingly, when the distal portion of the introducer sheath is introduced into a puncture site, the end portion formed at the acute angle hardly receives any stress from the puncture site, and it is possible to insert the end portion thereof into the puncture site without the end portion curling upward.

Furthermore, the distal portion of the introducer sheath includes the convex portion which is contiguous to the concave portion and is bent radially outward in the convex shape, and the convex portion is formed to have a sufficient wall thickness. Accordingly, it is possible to insert the end portion of the distal portion into the puncture site without the convex portion formed to have the sufficient thickness curling upward, contraction of the convex portion into a bellows shape, or twisting of the convex portion, even if the convex portion receives a larger stress from the puncture site after the end portion of the distal portion of the introducer sheath is inserted into the puncture site.

Here, in a case where the concave portion or the convex portion of the distal portion of the introducer sheath is formed in a shape which is bent in a quadratic curve shape, the following effect is exhibited. That is, it is possible to relieve the stress which the concave portion or the convex portion of the distal portion receives from the puncture site when the concave portion or the convex portion of the distal portion of the introducer sheath is introduced into the puncture site, by uniformly decentralizing the stress. Accordingly, it is possible to effectively prevent the curling upward due to the stress being concentrated on the concave portion or the convex portion in the distal portion when the concave portion or the convex portion of the distal portion of the introducer sheath is introduced into the puncture site.

Furthermore, in a case where the concave portion or the convex portion, which is bent in the quadratic curve shape, of the distal portion of the introducer sheath is bent in the parabola shape, the following effect is exhibited. That is, it is possible to relieve the stress which the concave portion or the convex portion of the distal portion receives from the puncture site when the concave portion or the convex portion of the distal portion of the introducer sheath is introduced into the puncture site, by uniformly decentralizing the stress along the external shape of the concave portion or the convex portion of the distal portion thereof. Accordingly, it is possible to effectively prevent the curling upward due to the stress being concentrated on the concave portion or the convex portion of the distal portion of the introducer sheath when the concave portion or the convex portion of the distal portion thereof is introduced into the puncture site.

Furthermore, the introducer assembly can be configured such that the inner diameter of the distal portion of the introducer sheath is smaller than the inner diameter of the main body portion of the introducer sheath before the dilator is inserted into the hollow portion (lumen) of the introducer sheath. When the dilator is inserted into the hollow portion of the introducer sheath and a distal end of the dilator protrudes from the distal end of the introducer sheath (at the time of an assembled state of the introducer assembly), the distal portion of the introducer sheath is configured to have the concave portion which is bent radially inward from the distal end (end portion) of the introducer sheath, in the concave shape in the cross section parallel to the axial direction, and the convex portion which is contiguous to the concave portion and is bent radially outward in the convex shape in the cross section parallel to the axial direction. That is, in the introducer assembly disclosed here, when the dilator is inserted into the hollow portion of the introducer sheath and the distal end of the dilator protrudes from the distal end of the introducer sheath (at the time of the assembled state of the introducer assembly), the inner diameter of the distal portion of the introducer sheath is increased to be larger than the outer diameter of the dilator. For this reason, in the assembled state of the introducer assembly in which the dilator is inserted into the hollow portion of the introducer sheath and the distal end of the dilator protrudes from the distal end of the introducer sheath, the distal portion of the introducer sheath has the concave portion which is bent radially inward from the distal end (end portion) of the introducer sheath, in the concave shape in the cross section parallel to the axial direction, and the convex portion which is contiguous to the concave portion and is bent radially outward in the convex shape in the cross section parallel to the axial direction. Accordingly, it is possible to prevent the distal portion of the introducer sheath from being curled upward when being introduced into the puncture site even if the wall thickness of the introducer sheath is made to be small.

Specifically, in the assembled state of the introducer assembly in which the dilator is inserted into the hollow portion of the introducer sheath and the distal end of the dilator protrudes from the distal end of the introducer sheath, the distal portion of the introducer sheath has the concave portion which is bent radially inward from the end portion of the distal portion thereof in the concave shape. Accordingly, at the end portion of the distal portion of the introducer sheath, in the cross section parallel to the axial direction, an outer surface of the introducer sheath is formed at an acute angle with respect to an inner surface of the introducer sheath. Accordingly, when an operator introduces the distal portion of the introducer sheath into the puncture site, the end portion formed at an acute angle hardly receives any stress from the puncture site, and it is possible to insert the end portion thereof into the puncture site without the end portion curling upward.

Furthermore, in the assembled state of the introducer assembly in which the dilator is inserted into the hollow portion of the introducer sheath and the distal end of the dilator protrudes from the distal end of the introducer sheath, the distal portion of the introducer sheath has the convex portion which is contiguous to the concave portion and is bent radially outward in the convex shape, and the convex portion is formed to have a sufficient thickness. Accordingly, it is possible to insert the end portion of the distal portion into the puncture site without the convex portion formed to have the sufficient thickness curling upward, contraction of the convex portion into a bellows shape, or twisting of the convex portion, even if the convex portion receives more stress from the puncture site after the end portion of the distal portion of the introducer sheath is inserted into the puncture site. In accordance with another aspect, an introducer assembly comprises: an elongated dilator possessing a distal end; and an elongated introducer sheath comprised of a tubular member that includes a distal portion and a main body portion which are both hollow and in which the elongated dilator is insertable so that a distal end of the dilator protrudes from an end portion of the distal portion, the distal portion possessing an inner diameter, and the main body portion possessing an inner diameter; the inner diameter of the distal portion is smaller than the inner diameter of the main body portion before the dilator is inserted into the hollow distal portion and the hollow main body portion. The distal portion of the introducer sheath possesses a tapering outer diameter and the main body portion possessing a constant outer diameter, and the outer surface of the distal portion of the introducer sheath and the outer surface of an adjacent portion of the main body portion are smoothly contiguous with each other in a curved shape without an inflection portion before the dilator is positioned in the introducer sheath such that the distal end of the dilator protrudes from the end portion of the distal portion. After the dilator is positioned in the introducer sheath such that the distal end of the dilator protrudes from the end portion of the distal portion, an external shape of the distal portion of the introducer sheath as seen in an axial cross-section possesses an external shape that includes a concave portion which is bent radially inward from the end portion in a concave shape in a cross section parallel to the axial direction, and a convex portion which is contiguous to the concave portion and is bent radially outward in a convex shape in the cross section parallel to the axial direction, with an inflection point between the concave portion and the convex portion.

DETAILED DESCRIPTION

Figure 1:
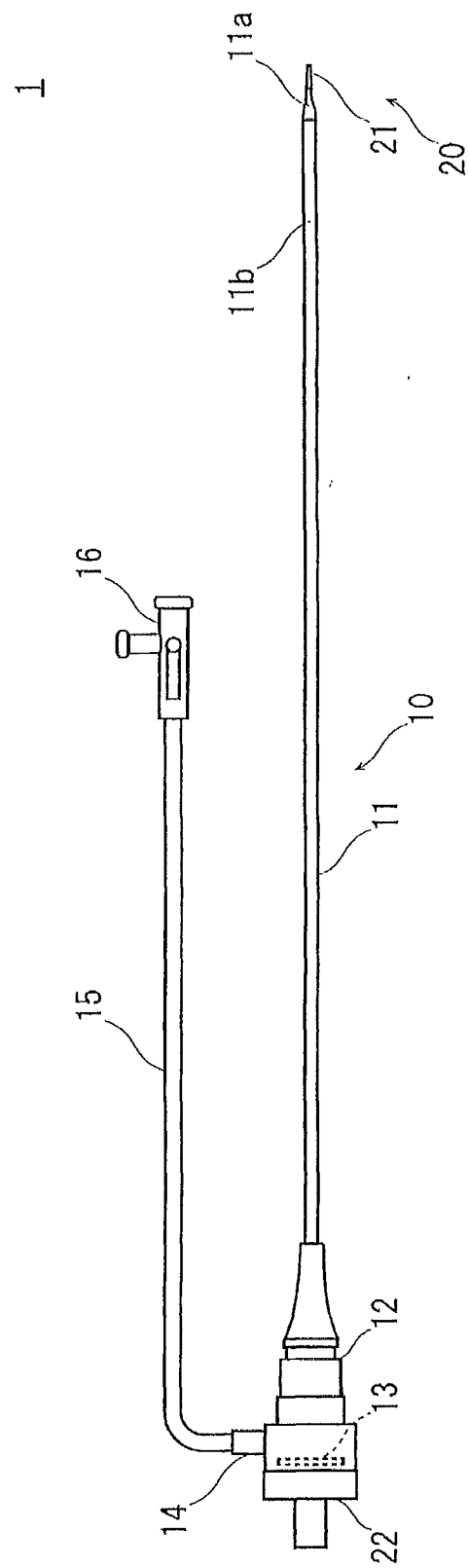
FIG. 1 is a plan view showing an introducer assembly to which is applied an introducer sheath according to an embodiment representing one example of the disclosed introducer sheath.

Hereinafter, an embodiment of an introducer sheath, and modifications, representing examples of the introducer sheath disclosed here will be described below with reference to the accompanying drawings. Common features are identified by the same reference numerals throughout the drawings and a detailed description of features previously described will not be repeated. In some cases, dimensional ratios in the drawings are exaggerated and may be different from the actual ratios for the convenience of description and understanding.

An introducer sheath 10 according is an instrument that ensures an access route into the lumen in a living body. The introducer sheath 10 remains in the lumen in a living body. A catheter for imaging which is a diagnostic instrument, or a balloon, a stent, or the like which is a therapeutic instrument is inserted into such an introducer sheath 10 and introduced into the lumen in a living body. In the description below, the hand operation unit side or end of the introducer assembly 1 from which the introducer assembly is operated will be referred to as a "proximal side" or "proximal end", and the side or end at which the introducer assembly is inserted into the lumen in a living body will be referred to as a "distal side" or "distal end".

First, the configuration of the introducer assembly 1 to which the introducer sheath 10 according to the present embodiment is applied will be specifically described with reference to FIGS. 1 to 5.

Figure 2:
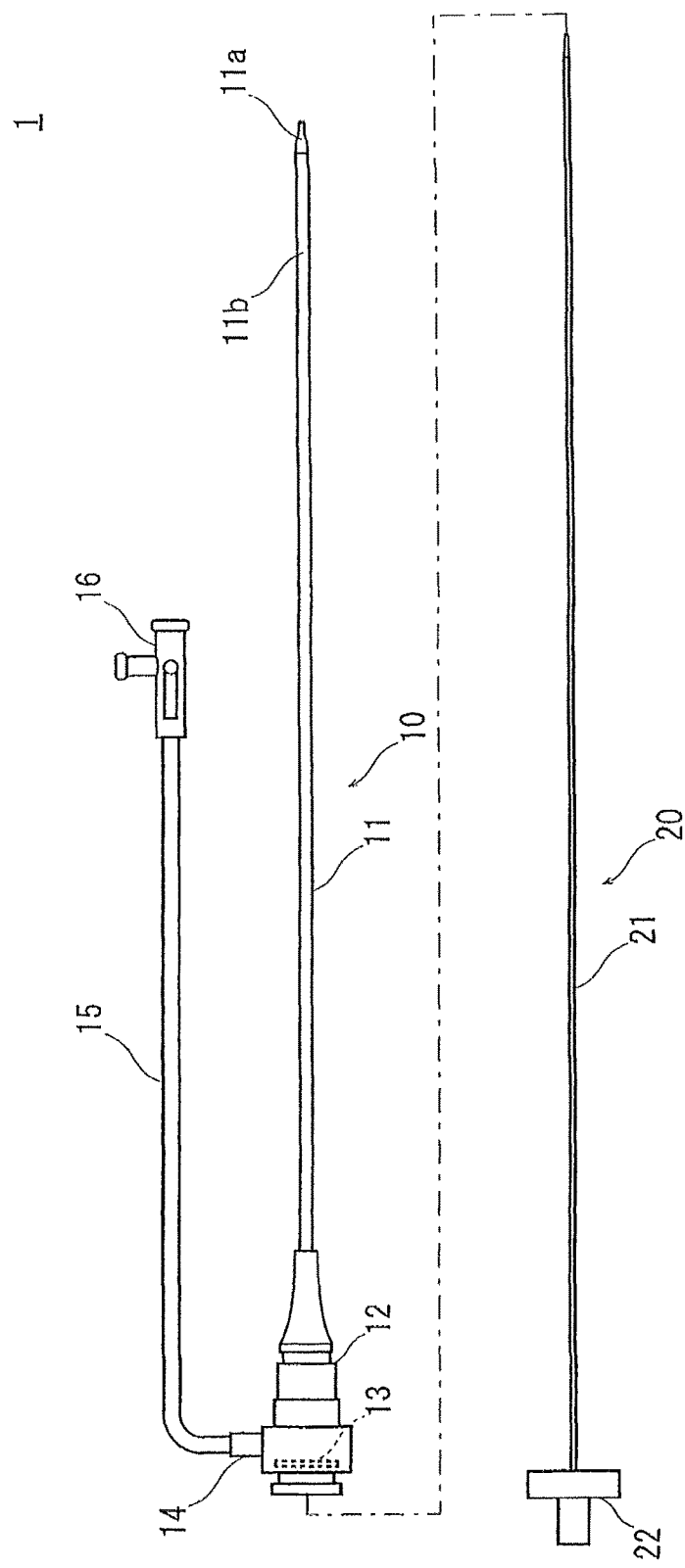
FIG. 2 is a plan view showing the introducer assembly after being disassembled into the introducer sheath and a dilator.

As shown in FIGS. 1 and 2, the introducer assembly 1 has an introducer sheath 10 that ensures an access route into the lumen in a living body; and a dilator 20 that assists in the percutaneous insertion of the introducer sheath 10 which remains in the lumen in the living body. The introducer assembly 1 is formed of or comprised of the introducer sheath 10 and the dilator 20. Here, the assembled state of the introducer assembly 1 is a state in which, as shown in FIG. 1, a distal end of the dilator 20 protrudes from (distally beyond) a distal end of the introducer sheath 10 by inserting the dilator 20 into a hollow portion of the introducer sheath 10 and connecting a sheath hub 12 with the dilator hub 22. That is, the introducer assembly 1 has a configuration in which the introducer sheath 10 and the dilator 20 are integrated with each other. Hereinafter, the introducer sheath 10 and the dilator 20 of the introducer assembly 1 will be described in detail.

The introducer sheath 10 ensures the access route into the lumen in a living body.

Specifically, after the introducer sheath 10 is placed in the lumen in the living body, a catheter for imaging which is a diagnostic instrument, or a balloon, a stent, or the like which is a therapeutic instrument is inserted into the introducer sheath and introduced into the lumen in the living body. Such an introducer sheath 10 is provided with, for example, a sheath tube 11, a sheath hub 12, a hemostasis valve 13, a side port 14, a tube 15, and a three-way stopcock 16. Hereinafter, each component provided in the introducer sheath 10 will be sequentially described.

The sheath tube 11 of the introducer sheath 10 is percutaneously placed in the lumen in a living body, and then, a catheter for imaging which is a diagnostic instrument, or a balloon, a stent, or the like which is a therapeutic instrument is inserted into the sheath tube 11 and introduced into the lumen in the living body. Such a sheath tube 11 is configured to possess, for example, an elongated tubular shape and a proximal side of the sheath tube is connected to a distal side of the sheath hub 12.

Figure 3:
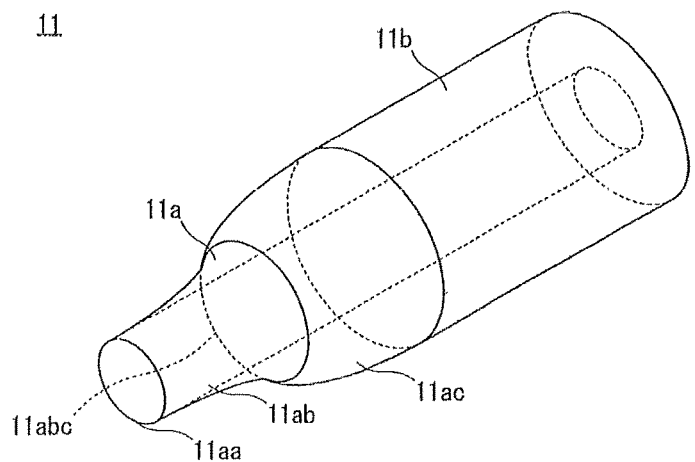
FIG. 3 is a perspective view showing a sheath tube of the introducer sheath.
Figure 4:
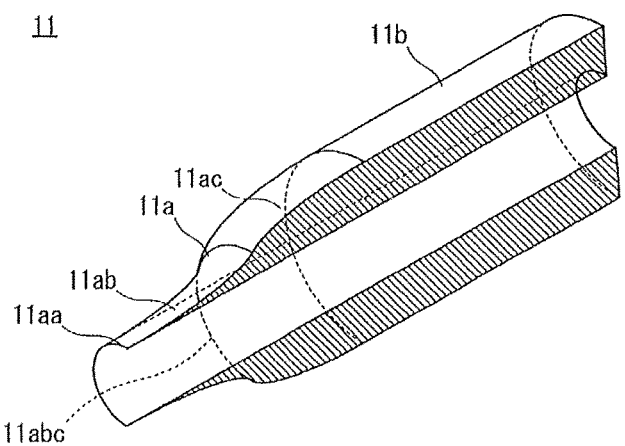
FIG. 4 is a perspective cross section showing the sheath tube of the introducer sheath.
Figure 5:
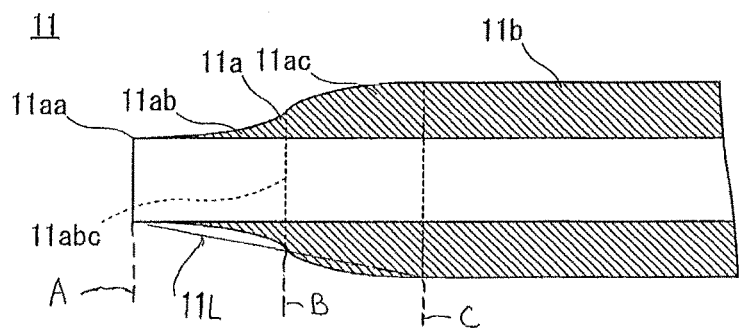
FIG. 5 is a plan view of view of a the cross section showing the sheath tube of the introducer sheath.

Here, as shown in FIGS. 3 to 5, the sheath tube 11 includes a distal portion 11a with a tapering outer diameter and a main body portion 11b with a constant outer diameter. Particularly, as shown in FIG. 5, the distal portion 11a of the sheath tube 11 is provided with a concave portion 11ab which is bent radially inward from an end portion 11aa, through which an elongated body (e.g., a dilator or other instrumentation) protrudes, in a concave shape when seen from a longitudinal (axial) cross section parallel to an axial direction; and a convex portion 11ac which is contiguous to the concave portion 11ab and is bent radially outward in a convex shape when seen from a longitudinal (axial) cross section parallel to the axial direction. More specifically, the concave portion 11ab is in the section between A and B, is located under the straight line extending from A to B, and in the longitudinal cross-section shown possesses a radially inward curvature relative to the straight line between A and B. The convex portion 11ac is in the section between B and C, is located above the straight line extending from B to C, and in the longitudinal cross-section shown possesses a radially outward curvature relative to the straight line between B and C. In the distal portion 11a, the proximal side of the concave portion 11ab and the distal side of the convex portion 11ac are formed so as to be smoothly contiguous with each other through an inflection portion (annular inflection line) 11abc. Furthermore, the external shape of the concave portion 11ab or the convex portion 11ac of the sheath tube 11 is, as shown in FIG. 4, bent in a quadratic curve shape. In addition, the external shape of the concave portion 11ab or the convex portion 11ac, which is bent in the quadratic curve shape, of the sheath tube 11 is, for example, a parabola shape.

In addition, the sheath tube 11 can be formed of a polymeric material such as polyolefin (for example, polyethylene, polypropylene, polybutene, ethylene-propylene copolymers, ethylene-vinyl acetate copolymers, ionomers, or a mixture of two or more thereof), polyolefin elastomer, cross-linked bodies of polyolefin, polyvinyl chloride, polyamide, polyamide elastomer, polyester, polyester elastomer, polyurethane, polyurethane elastomer, fluorine resin, polycarbonate, polystyrene, polyacetal, polyimide, polyetherimide, and aromatic polyether ketone, a mixture thereof, or the like. Furthermore, the sheath tube 11 is preferably formed of an ethylene-tetrafluoroethylene copolymer (ETFE), but the material is not limited thereto.

The sheath hub 12 of the introducer sheath 10 internally communicates with the sheath tube 11 and the side port 14 and has the hemostasis valve 13. Such a sheath hub 12 is configured to possess, for example, a rectangular shape which is hollow inside, and is connected to the proximal end of the sheath tube 11. Here, the distal end of the sheath hub 12 is provided with, for example, a kink prevention member formed of soft resin to buffer any curve of the introducer sheath 10 using the kink prevention member. In addition, the sheath hub 12, exclusive of the kink prevention member, is preferably formed of hard resin such as polyolefin such as polyethylene and polypropylene, polyamide, polycarbonate, and polystyrene, but the material is not limited to these materials.

The hemostasis valve 13 of the introducer sheath 10 stops blood flowing out from the inside of the blood vessel through the sheath tube 11. Such a hemostasis valve 13 is configured to possess, for example, an approximately oval shape and is fixed to the inside of the sheath hub 12 in a state of being liquid-tight. In addition, the hemostasis valve 13 is preferably formed of silicone rubber, latex rubber, butyl rubber, isoprene rubber, and the like which have elasticity, but the material is not limited thereto.

The side port 14 of the introducer sheath 10 communicates with the sheath tube 11 and the tube 15. Such a side port 14 is formed in, for example, a cylindrical shape, and one end of the side port is connected to the sheath tube 11 and the other end of the side port is liquid-tightly connected to the tube 15.

The tube 15 of the introducer sheath 10 communicates with the side port 14 and the three-way stopcock 16. Such a tube 15 is configured to possess, for example, a bendable cylindrical shape, and one end of the tube 15 is connected to the side port 14 and the other end of the tube 15 is liquid-tightly connected to the three-way stopcock 16. In addition, the tube 15 is preferably formed of, for example, polybutadiene having flexibility, but the material forming the tube 15 is not limited to this material.

The three-way stopcock 16 of the introducer sheath 10 allows injection of, for example, liquid such as physiological saline to the introducer sheath 10 through the tube 15 and the side port 14. Such a tube 15 is configured to possess a cylindrical shape and one end of the tube 15 is connected to the side port 14.

The dilator 20 assists in the percutaneous insertion of the introducer sheath 10 which remains in the lumen in a living body.

Specifically, the dilator 20 prevents the sheath tube 11 from being bent when inserting the sheath tube 11 of the introducer sheath 10 into the blood vessel by increasing the diameter of a perforation of the skin. Such a dilator 20 is provided with, for example, a dilator tube 21 and a dilator hub 22. Hereinafter, each component provided in the dilator 20 will be sequentially described.

The dilator tube 21 of the dilator 20 is inserted into the sheath tube 11 and assists in the percutaneous insertion of the introducer sheath 10 which remains in the lumen in a living body. That is, the dilator tube 21 inserted into the sheath tube 11 is, as shown in FIG. 1, in a state in which a distal end of the dilator tube 21 protrudes from a distal end of the sheath tube 11. Such a dilator tube 21 is configured to possess, for example, an elongated tubular shape and the proximal end of the dilator tube 21 is connected to a distal end of the dilator hub 22.

In addition, the dilator tube 21 can be formed of a polymeric material such as polyolefin (for example, polyethylene, polypropylene, polybutene, ethylene-propylene copolymers, ethylene-vinyl acetate copolymers, ionomers, or a mixture of two or more thereof), polyolefin elastomer, cross-linked bodies of polyolefin, polyvinyl chloride, polyamide, polyamide elastomer, polyester, polyester elastomer, polyurethane, polyurethane elastomer, fluorine resin, polycarbonate, polystyrene, polyacetal, polyimide, polyetherimide, and aromatic polyether ketone, a mixture thereof, or the like.

The dilator hub 22 of the dilator 20 detachably holds the dilator tube 21 with respect to the sheath hub 12. Such a dilator hub 22 is configured to possess, for example, a stepped columnar shape and is connected to the proximal side of the dilator tube 21. In addition, it is preferable that the sheath hub 12 be formed of hard resin such as polyolefin such as polyethylene and polypropylene, polyamide, polycarbonate, and polystyrene, but the material is not limited thereto.

Next, the verification result relating to the prevention of the occurrence of the curling upward in the introducer sheath 10 according to the present embodiment will be specifically described with reference to FIG. 6 and Table 1.

Figure 6A:
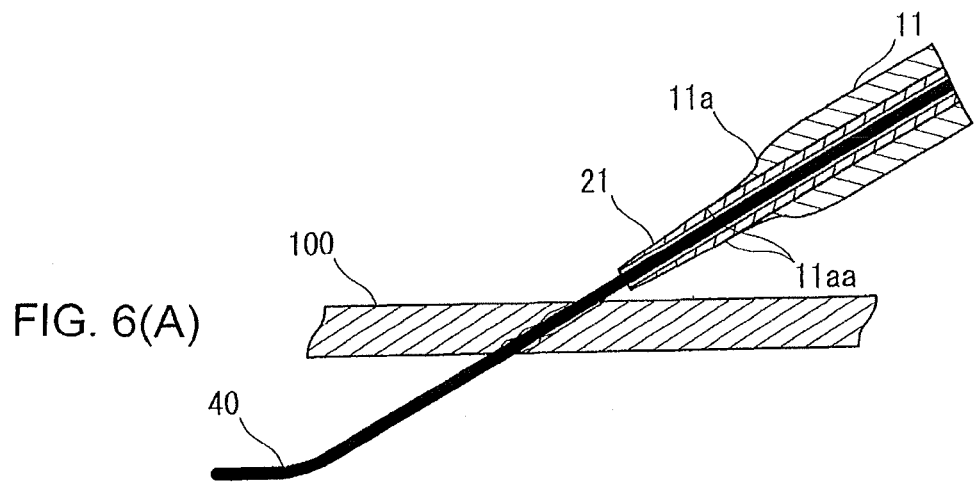
FIGS. 6(A)-6(C) are schematic views showing a method of verifying or denying the occurrence of curling upward in a distal portion of the introducer sheath by inserting the introducer assembly into a film for puncturing test, in order of FIG. 6(A) to FIG. 6(C).
Figure 6B:
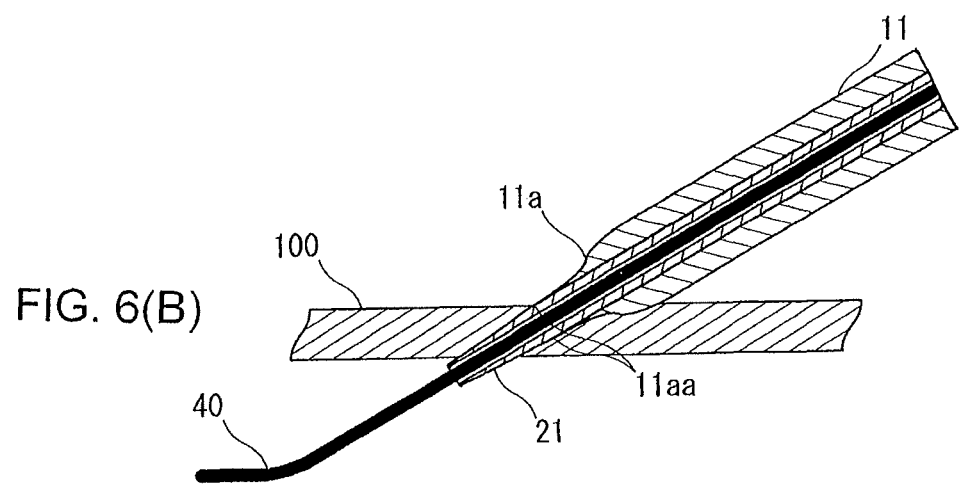
Figure 6C:
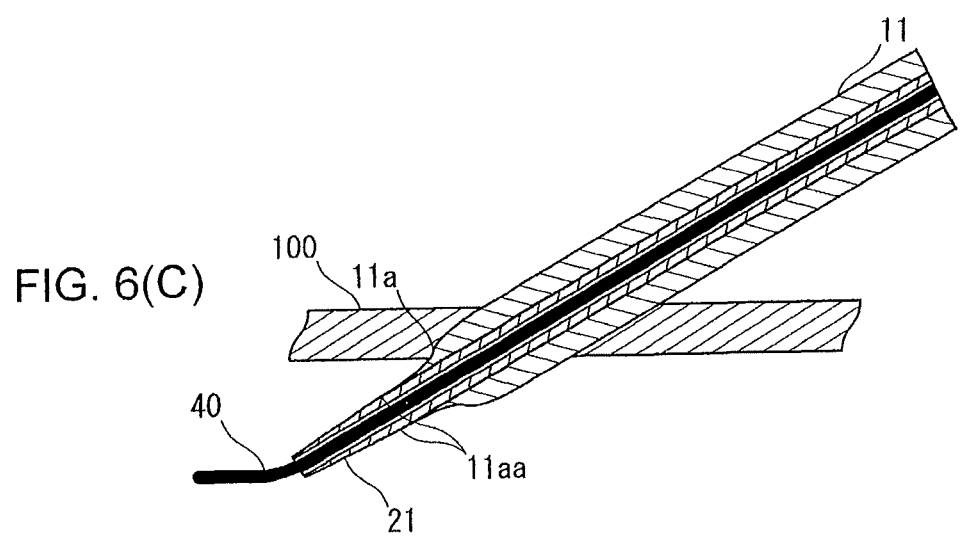

FIG. 6 schematically illustrates a method of verifying or denying the occurrence of curling upward in a distal portion 11a of the sheath tube 11 of the introducer sheath 10 by inserting the introducer assembly into a film 100 (hereinafter referred to as the film for puncturing test) which is made of cowhide, in order of FIG. 6(A) to FIG. 6(C).

FIG. 6(A) shows a state immediately before inserting the introducer assembly 1 into the film 100 for puncturing test. Here, although it is not shown, the film 100 for puncturing test is punctured using a puncture needle at an angle of 30 degrees. Subsequently, the puncture needle is removed and a guide wire 40 is inserted in the hole in the film 100. In addition, the introducer assembly 1 is inserted into the film 100 for puncturing test at the angle of 30 degrees (relative to the film 100) along the guide wire 40.

The FIG. 6(B) shows a state in the middle of insertion of the introducer assembly 1 into the film 100 for puncturing test, during which the distal portion 11a of the sheath tube 11 comes into contact with the film 100 for puncturing test. Here, as shown in FIG. 6(B), while the distal portion 11a of the sheath tube 11 comes into contact with the film 100 for puncturing test and a load is applied to the distal portion 100 of the sheath tube 11, there is no occurrence of upward curling.

FIG. 6(C) illustrates a state in which the insertion of the introducer assembly 1 into the film 100 for puncturing test is completed, and the distal portion 11a of the sheath tube 11 penetrates the film 100 for puncturing test. Here, as shown in FIG. 6(C), while the distal portion 11a of the sheath tube 11 penetrates the film 100 for puncturing test and a load is applied to the distal portion 100 of the sheath tube 11, there is no occurrence of upward curling.

As shown in Table 1, the verification shown in FIGS. 6(A) to 6(C) was performed 7 times for the introducer sheath 10 according to the present embodiment, and a sheath according to a comparison example of which the external shape at a distal portion of a sheath tube is formed in a linearly tapered shape. In the case of the introducer sheath 10 according to the present embodiment, the upward curling of /the distal portion 11a of the sheath tube 11 was not visually confirmed in the verification operations performed 7 times in total. In contrast, in the case of the sheath according to the comparative example, the upward curling of the distal portion of the sheath tube was visually confirmed in the verification operations performed 7 times in total, except for the fifth verification.

TABLE 1

|  |  | Sheath according to present embodiment | Sheath according to Comparative Example |
|---|---|---|---|
| Measurement (n = 7) | 1 | ◯ | X |
|  | 2 | ◯ | X |
|  | 3 | ◯ | X |
|  | 4 | ◯ | X |
|  | 5 | ◯ | ◯ |
|  | 6 | ◯ | X |
|  | 7 | ◯ | X |

◯: Curling is not confirmed
X: Curling is confirmed

Here, a sheath tube 31 which is a first modification example according to the sheath tube 11 of the introducer sheath 10 according to the present embodiment will be described with reference to FIGS. 7 to 9.

Figure 7:
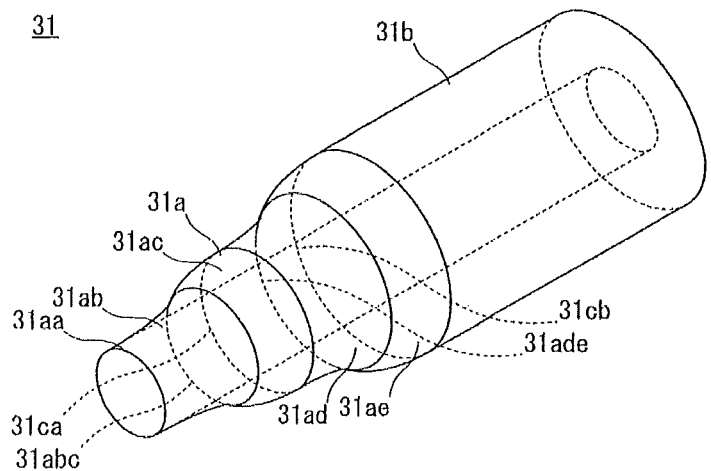
FIG. 7 is a perspective view showing a first modification example of the sheath tube of the introducer sheath.
Figure 8:
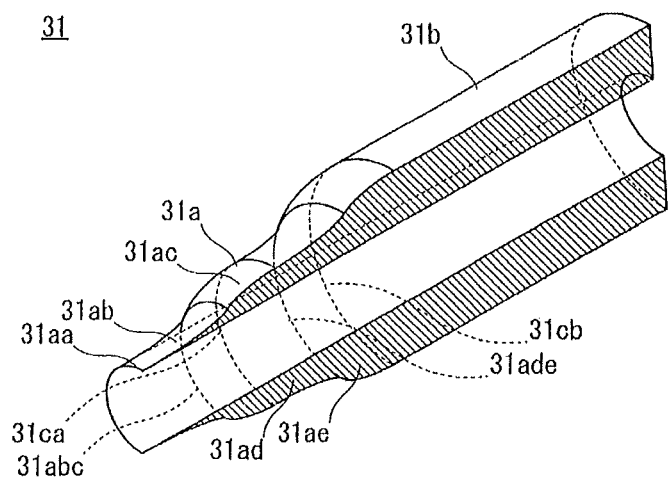
FIG. 8 is a perspective view of a cross section showing the first modification example of the sheath tube of the introducer sheath.
Figure 9:
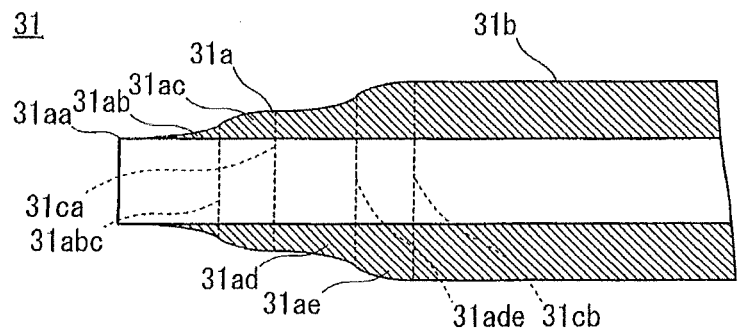
FIG. 9 is a plan view of a cross section showing the first modification example of the sheath tube of the introducer sheath.

As shown in FIGS. 7 to 9, the sheath tube 31 is formed of a distal portion 31a with a tapering outer diameter and a main body portion 31b with a constant outer diameter. The distal portion 31a of the sheath tube 31 is provided with a concave portion 31ab which is bent radially inward from an end portion 31aa, through which an elongated body protrudes, in a concave shape when seen from a cross section parallel to an axial direction; and a convex portion 31ac which is contiguous to the concave portion 31ab and is bent radially outward in a convex shape when seen from a cross section parallel to an axial direction. In the distal portion 31a, the proximal side of the concave portion 31ab and the distal side of the convex portion 31ac are formed so as to be smoothly contiguous with each other through an inflection portion (annular inflection line) 31abc. Furthermore, the distal portion 31a of the sheath tube 31 is provided with a concave portion 31ad which is bent radially inward from an inflection portion 31ca, which is positioned at a proximal side of the convex portion 31ac and of which the angle is parallel to the axial direction, in a concave shape; and a convex portion 31ae which is contiguous to the concave portion 31ad and is bent radially outward in a convex shape. In the distal portion 31a, the proximal side of the concave portion 31ad and the distal side of the convex portion 31ae are formed so as to be smoothly contiguous with each other through an inflection portion (annular inflection line) 31ade. Here, an inflection portion (annular inflection line) 31cb which is positioned at the proximal side of the convex portion 31ae and of which the angle is parallel to the axial direction is contiguous to the main body portion 31b. In a case where the concave portion and the convex portion which are provided in the distal portion of the sheath tube in this manner are set as a pair, the number of pairs is not particularly limited. That is, it is possible to configure the distal portion of the sheath tube 31 to include more than the two pairs of concave and convex portions shown in FIGS. 7-9.

Here, a sheath tube 41 which is a second modification example of the sheath tube 11 of the introducer sheath 10 according to the present embodiment will be described with reference to FIGS. 10 and 11.

Figure 10:
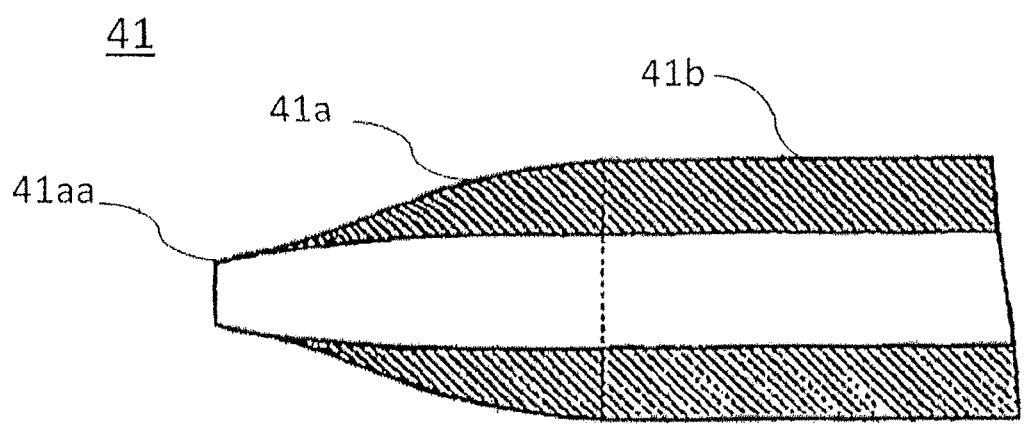
FIG. 10 is a plan view of a cross section which shows a second modification example of the sheath tube of the introducer sheath and shows a state in which the introducer assembly is disassembled into the introducer sheath and the dilator.

FIG. 10 is a longitudinal or axial cross-sectional view showing the sheath tube 41 of the introducer sheath 10 before the dilator 20 is inserted into the lumen of the introducer sheath 10 (in a state in which the introducer assembly 1 is disassembled into the introducer sheath 10 and the dilator 20 as shown in FIG. 2). In addition, FIG. 11 is a cross-sectional view showing the sheath tube 41 of the introducer sheath 10 in a state in which the dilator 20 is inserted into the lumen of the introducer sheath 10 (an assembled state of the introducer assembly 1 as shown in FIG. 1).

The sheath tube 41 is formed of, as shown in FIG. 10, a distal portion 41a with a tapering outer diameter and a main body portion 41b with a constant outer diameter in a state before the dilator 20 is inserted into the lumen of the introducer sheath 10. That is, the sheath tube 41 has a distal portion 41a and a main body portion 41b, and a proximal end of the distal portion 41a is connected to a distal end of the main body portion 41b. On the other hand, an end portion 41aa through which an elongated body (e.g., dilator or other instrumentation) protrudes and the proximal end of the distal portion 41a are smoothly contiguous with each other in a curved shape without having an inflection portion 41abc as shown in FIG. 11. Here, the inflection portion is a change portion where a concave portion which is bent radially inward in a concave shape is changed to a convex portion which is bent radially outward in a convex shape (for example, the inflection portion 41abc shown in FIG. 11). The sheath tube 41 shown in FIG. 10 is not particularly limited as long as the end portion 41aa, through which an elongated body (e.g., dilator or other instrumentation) protrudes, and the proximal side of the main body portion 41b are contiguous with each other without having the inflection portion 41abc as shown in FIG. 11. For example, the end portion and the proximal side of the main body portion may be linearly contiguous. In addition, the lumen of the distal portion 41a of the sheath tube 41 is tapered from the proximal end to the distal end of the distal portion 41a. The inner diameter of the distal portion is thus smaller than the inner diameter/ of the main body portion before the dilator (i.e., before any item) is inserted into the hollow portion of the introducer sheath. Specifically, the inner diameter of the end portion 41aa of the distal portion 41a of the introducer sheath 10 is configured to be smaller than the inner diameter of the main body portion 41b of the introducer sheath 10. The tapering inner diameter begins at the distal side of the dotted line in FIG. 10.

Figure 11:
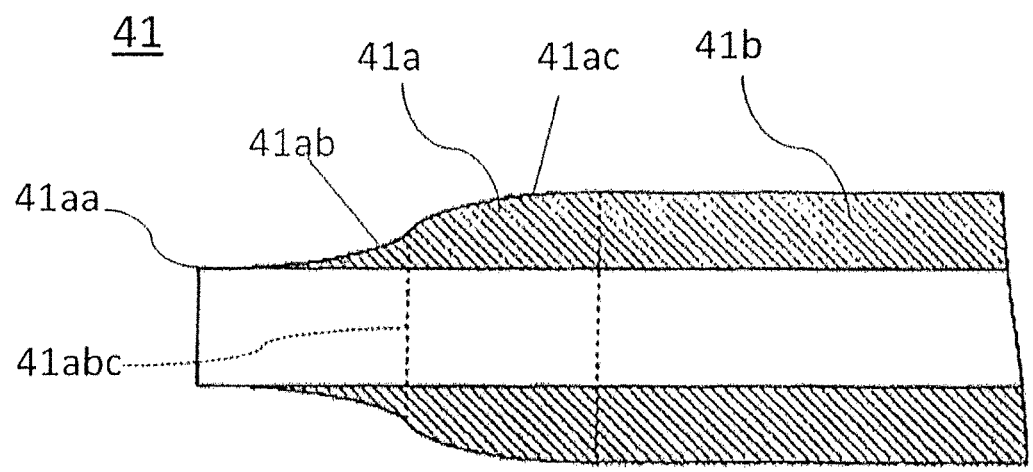
FIG. 11 is a plan view of a cross section which shows the second modification example of the sheath tube of the introducer sheath and shows an assembled state of the introducer assembly in which the dilator is positioned in the lumen of the sheath, except the dilator is omitted.

FIG. 11 shows the sheath tube 41 in a state in which the dilator 20 is inserted into (positioned in) the lumen of the introducer sheath 10 and moved (advanced) so that the distal end of the dilator 20 protrudes from the distal end of the introducer sheath 10, that is, in a state where the introducer sheath 10 and the dilator 20 are integrated (the assembled state of the introducer assembly). The distal portion 41a of the sheath tube 41 shown in FIG. 11 is provided with a concave portion 41ab which is bent radially inward from the end portion 41aa, through which an elongated body protrudes, in a concave shape when seen from the longitudinal (axial) cross section parallel to the axial direction; and a convex portion 41ac which is contiguous to the concave portion 41ab and is bent radially outward in a convex shape when seen from the longitudinal (axial) cross section parallel to the axial direction. That is, in the distal portion 41a, the proximal side of the concave portion 41ab and the distal side of the convex portion 41ac are configured to be smoothly contiguous with each other through an inflection portion 41abc. That is, in the introducer sheath 10 of the second modification example, in the assembled state of the introducer assembly as shown in FIG. 1, the distal portion 41a of the introducer sheath 10 has a concave portion which is bent radially inward from the end portion, through which the dilator 20 protrudes, in a concave shape in the longitudinal (axial) cross section parallel to the axial direction; and a convex portion which is contiguous to the concave portion and is bent radially outward in a convex shape, in the longitudinal (axial) cross section parallel to the axial direction. Accordingly, the introducer sheath 10 can prevent the distal portion 41a from being curled upward when being introduced into a puncture site even if the wall thickness of the distal portion 41a of the sheath tube 41 is made small in the introducer assembly. The introducer sheath 10 of the second modification example has a small wall thickness in the distal portion 41a of the sheath tube 41 and flexibility. Therefore, when the distal end of the dilator 20 protrudes from (distally beyond) the distal end of the introducer sheath 10, the inner diameter of the end portion 41aa of the distal portion 41a of the introducer sheath 10 is increased by the outer diameter portion of the dilator 20 and the end portion 41aa is deformed in the shape shown in FIG. 11.

According to the above-described present embodiment, the following effect is exhibited.

According to the present embodiment, it is possible to prevent the distal portion from being curled upward when being introduced into a puncture site even if the wall thickness of the distal portion is small, with the distal portion 11a of the sheath tube 11 of the introducer sheath 10 including the concave portion which is bent radially inward from the end portion, through which an elongated body protrudes, in the concave shape in the cross section parallel to the axial direction, and the convex portion which is contiguous to the concave portion and is bent radially outward in the convex shape in the cross section parallel to the axial direction.

That is, according to the present embodiment, the distal portion 11a of the sheath tube 11 includes the concave portion 11ab which is bent radially inward from the end portion 11aa thereof in the concave shape, and therefore, the end portion 11aa is formed at an acute angle. Accordingly, when the distal portion 11a of the sheath tube 11 is introduced into a puncture site, the end portion 11aa formed at the acute angle hardly receives any stress from the puncture site, and it is possible to insert the end portion of the sheath tube into the puncture site without the curling upward of the end portion 11aa. Furthermore, the distal portion 11a of the sheath tube 11 includes the convex portion 11ac which is contiguous to the concave portion 11ab and is bent radially outward in the convex shape, and the convex portion 11ac is formed to have a sufficient wall thickness. Accordingly, it is possible to insert the distal portion into the puncture site without curling upward of the convex portion 11ac formed to have the sufficient wall thickness, contraction of the convex portion into a bellows shape, or twisting of the convex portion, even if the convex portion 11ac receives more stress from the puncture site after the end portion 11aa of the distal portion 11a of the sheath tube 11 is inserted into the puncture site.

Furthermore, according to the present embodiment, the external shape of the concave portion 11ab or the convex portion 11ac of the distal portion 11a of the sheath tube 11 of the introducer sheath 10 can be made to a shape which is bent in a quadratic curve shape. If the shape of the concave portion 11ab or the convex portion 11ac of the distal portion 11a of the sheath tube 11 is formed in this way, it is possible to relieve the stress which the concave portion 11ab or the convex portion 11ac of the distal portion 11a receives from the puncture site when the concave portion 11ab or the convex portion 11ac of the distal portion 11a of the sheath tube 11 is introduced into the puncture site, by uniformly decentralizing the stress. Accordingly, it is possible to efficiently prevent the curling upward due to the stress being concentrated on the concave portion 11ab or the convex portion 11ac of the distal portion 11a when the concave portion 11ab or the convex portion 11ac of the distal portion 11a of the sheath tube 11 is introduced into the puncture site.

In addition, according to the present embodiment, it is possible to make the external shape of the concave portion 11ab or the convex portion 11ac, which is bent in the quadratic curve shape, of the distal portion 11a of the sheath tube 11 of the introducer sheath 10 be bent in a parabola (parabolic) shape. If the shape of the concave portion 11ab or the convex portion 11ac of the distal portion 11a of the sheath tube 11 is formed in this way, it is possible to relieve the stress which the concave portion 11ab or the convex portion 11ac of the distal portion 11a receives from the puncture site when the concave portion 11ab or the convex portion 11ac of the distal portion 11a of the sheath tube 11 is introduced into the puncture site, by uniformly decentralizing the stress along the external shape of the concave portion 11ab or the convex portion 11ac of the distal portion 11a. Accordingly, it is possible to efficiently prevent the curling upward due to the stress being concentrated on the concave portion 11ab or the convex portion 11ac of the distal portion 11a when the concave portion 11ab or the convex portion 11ac of the distal portion 11a of the sheath tube 11 is introduced into the puncture site.

The detailed description above describes embodiments of an introducer sheath representing examples of the introducer sheath of the present invention. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:
1. An introducer assembly comprising:
an elongated dilator possessing a distal end;
an elongated introducer sheath comprised of a tubular member possessing a hollow portion into which the elongated dilator is freely insertable, the introducer sheath extending in an axial direction, the introducer sheath including a distal portion possessing a tapering outer diameter, and a main body portion located proximally of the distal portion, the main body portion and the distal portion possessing an inner diameter;

the inner diameter of the distal portion is smaller than the inner diameter of the main body portion before the dilator is inserted into the hollow portion of the introducer sheath; and when the dilator is inserted into the hollow portion of the introducer sheath and the distal end of the dilator protrudes from an end portion of the distal portion through which the elongated dilator protrudes, the distal portion possessing an external shape including a concave portion which is bent radially inward from the end portion in a concave shape in a cross section parallel to the axial direction, and a convex portion which is contiguous to the concave portion and is bent radially outward in a convex shape in the cross section parallel to the axial direction.

2. The introducer sheath according to claim 1, wherein an external shape of the concave portion or the convex portion is a shape which is bent in a quadratic curve shape.

3. The introducer sheath according to claim 2, wherein the external shape which is bent in the quadratic curve shape is a parabolic shape.

4. An introducer assembly comprising:
an elongated dilator possessing a distal end;
an elongated introducer sheath comprised of a tubular member that includes a distal portion and a main body portion which are both hollow and in which the elongated dilator is insertable so that a distal end of the dilator protrudes from an end portion of the distal portion, the distal portion possessing an inner diameter, and the main body portion possessing an inner diameter;

the inner diameter of the distal portion is smaller than the inner diameter of the main body portion before the dilator is inserted into the hollow distal portion and the hollow main body portion;

the distal portion of the introducer sheath possessing a tapering outer diameter and the main body portion possessing a constant outer diameter;

an outer surface of the distal portion of the introducer sheath and an outer surface of an adjacent portion of the main body portion being smoothly contiguous with each other in a curved shape without an inflection portion before the dilator is positioned in the introducer sheath such that the distal end of the dilator protrudes from the end portion of the distal portion; and after the dilator is positioned in the introducer sheath such that the distal end of the dilator protrudes from the end portion of the distal portion, an external shape of the distal portion of the introducer sheath as seen in an axial cross-section possesses an external shape that includes a concave portion which is bent radially inward from the end portion in a concave shape in a cross section parallel to the axial direction, and a convex portion which is contiguous to the concave portion and is bent radially outward in a convex shape in the cross section parallel to the axial direction, with an inflection point between the concave portion and the convex portion.

5. The introducer sheath according to claim 4, wherein an external shape of the concave portion or the convex portion is a shape which is bent in a quadratic curve shape.

6. The introducer sheath according to claim 5, wherein the external shape which is bent in the quadratic curve shape is a parabolic shape.

* * * * *